US011594308B2

(12) United States Patent
Bex et al.

(10) Patent No.: US 11,594,308 B2
(45) Date of Patent: Feb. 28, 2023

(54) METHOD AND SYSTEM FOR ADAPTIVE SCHEDULING OF CLINICAL ASSESSMENTS

(71) Applicants: Northeastern University, Boston, MA (US); The Schepens Eye Research Institute, Inc., Boston, MA (US)

(72) Inventors: Peter John Bex, Concord, MA (US); John F. Ackermann, Boston, MA (US); Tobias Elze, Boston, MA (US)

(73) Assignees: NORTHEASTERN UNIVERSITY, Boston, MA (US); THE SCHEPENS EYE RESEARCH INSTITUTE, INC., Boston, MA (US)

( * ) Notice: Subject to any disclaimer, the term of this patent is extended or adjusted under 35 U.S.C. 154(b) by 1213 days.

(21) Appl. No.: 15/735,788

(22) PCT Filed: Jun. 16, 2016

(86) PCT No.: PCT/US2016/037880
§ 371 (c)(1),
(2) Date: Dec. 12, 2017

(87) PCT Pub. No.: WO2016/205521
PCT Pub. Date: Dec. 22, 2016

(65) Prior Publication Data
US 2018/0190380 A1   Jul. 5, 2018

Related U.S. Application Data

(60) Provisional application No. 62/180,778, filed on Jun. 17, 2015.

(51) Int. Cl.
*G16H 40/67* (2018.01)
*G16H 50/20* (2018.01)
(Continued)

(52) U.S. Cl.
CPC ............. *G16H 10/40* (2018.01); *G16H 40/20* (2018.01); *G16H 40/40* (2018.01); *G16H 40/60* (2018.01);
(Continued)

(58) Field of Classification Search
CPC .... G16H 10/00–80/00; G06F 1/00–2221/2153
See application file for complete search history.

(56) References Cited

U.S. PATENT DOCUMENTS 9,883,809 B2 * 2/2018 Klap .................. A61B 5/746
2008/0301077 A1 * 12/2008 Fung .................. G16H 50/20
706/46

(Continued)

FOREIGN PATENT DOCUMENTS

| CN | 104605939 A | * | 5/2015 | ........... A61B 5/0002 |
| WO | WO 2013/170091 A1 | | 11/2013 | |
| WO | WO 2016/205521 A1 | | 12/2016 | |

OTHER PUBLICATIONS

Lin et al., "Accuracy Based Adaptive Sampling and Multi-Sensor Scheduling for Collaborative Target Tracking," Ninth International Conference on Control, Automation, Robotics and Vision, ICARCV 2006. (Year: 2016).*

(Continued)

*Primary Examiner* — Jonathon A. Szumny
(74) *Attorney, Agent, or Firm* — Hamilton, Brook, Smith & Reynolds, P.C.

(57) ABSTRACT

Methods and systems providing adaptive assessment of a physical subject to efficiently collect assessment data and modify an assessment schedule based on the analyses. The methods and systems can control the timing of each assessment in order to collect data at times and under conditions that are most informative about the physical subject. Such adaptive methods and systems significantly minimize the frequency of data collection without loss in accuracy or (Continued)

precision and can increase test reliability through reduction in redundancy. The ability to estimate an unknown, underlying function using a small number of free parameters that remain constant regardless of the number of data points being estimated substantially reduces the error of the function estimate. Because estimates of the measurement error are achieved with a minimum of sampled assessments, and with great accuracy, the statistical power of clinical trials, for example, can be greatly increased.

18 Claims, 15 Drawing Sheets

(51) Int. Cl.
*G16H 40/20* (2018.01)
*G16H 50/70* (2018.01)
*G16H 10/40* (2018.01)
*G16H 40/40* (2018.01)
*G16H 40/60* (2018.01)

(52) U.S. Cl.
CPC ............. *G16H 40/67* (2018.01); *G16H 50/20* (2018.01); *G16H 50/70* (2018.01)

(56) References Cited

U.S. PATENT DOCUMENTS

| | | | | |
|---|---|---|---|---|
| 2011/0004110 | A1* | 1/2011 | Shusterman | G16H 50/20 600/509 |
| 2013/0116999 | A1* | 5/2013 | Stein | G16H 50/50 703/11 |
| 2014/0280145 | A1* | 9/2014 | Heit | G06F 16/285 707/737 |
| 2015/0164416 | A1* | 6/2015 | Nothacker | A61B 5/0022 340/573.1 |
| 2018/0025110 | A1* | 1/2018 | Meuleman | G16B 20/00 702/19 |
| 2021/0151184 | A1* | 5/2021 | Yuen | A61B 5/112 |

OTHER PUBLICATIONS

Willett et al. "Backcasting: Adaptive Sampling for Sensor Networks," Information Processing in Sensor Networks 2004, pp. 124-133. (Year: 2004).*

Craven et al., "Compressed Sensing for Bioelectric Signals: A Review," IEEE Journal of Biomedical and Health Informatics, vol. 19, No. 2, Mar. 2015 (Year: 2015).*

Hardwick et al., "Flexible Algorithms for Creating and Analyzing Adaptive Sampling Procedures," New Developments and Applications in Experimental Design—IMS Lecture Nodes—Monograph Series (1998) vol. 24, pp. 91-105. (Year: 1998).*

Benda et al., "From response to stimulus: adaptive sampling in sensory physiology," Current Opinion in Neurobiology, 2007, 17: 430-436. (Year: 2007).*

Bohs et al., Real-time adaptive sampling with the fan algorithm, Med. & Biol. Eng. & Comput., 1988, 26, 565-573. (Year: 1988).*

Thomas A. Lasko, "Nonstationary Gaussian Process Regression for Evaluating Clinical Laboratory Test Sampling Strategies", Proc Conf AAAI Artif Intell., 2015, Jan. 1, 2015, pp. 1777-1783.

International Search Report and Written Opinion of the International Searching Authority for International Application No. PCT/US2016/037880, entitled "Method And System For Adaptive Scheduling Of Clinical Assessments", dated Sep. 29, 2016.

Singh, et al., "Active Learning for Sampling in Time-Series Experiments With Application to Gene Expression Analysis", Proceedings of the 22nd International Conference on Machine Learning, pp. 832-839, Bonn, Germany, 2005.

Poppe, et al., "A predictive approach to nonparametric inference for adaptive sequential sampling of psychophysical experiments", Journal of Mathematical Psychology 56 (2012) 179-195.

International Preliminary Report on Patentability and Written Opinion of the International Searching Authority for International Application No. PCT/US2016/037880, entitled "Method And System For Adaptive Scheduling Of Clinical Assessments", dated Dec. 19, 2017.

* cited by examiner

METHOD AND SYSTEM FOR ADAPTIVE SCHEDULING OF CLINICAL ASSESSMENTS

RELATED APPLICATIONS

This application is the U.S. National Stage of International Application No. PCT/US2016/037880, filed Jun. 16, 2016, which designates the U.S., is published in English, and claims the benefit of U.S. Provisional Application No. 62/180,778, filed on Jun. 17, 2015. The entire teachings of the above applications are incorporated herein by reference.

BACKGROUND

Ecological Momentary Assessment (EMA) data provide a rich context for diagnosis and tracking of the progression or remediation of disease during health care interventions. EMA involves frequent data collection between clinical appointments and in non-clinical settings and, when implemented on mobile systems, provide a platform for real-time delivery of behavioral therapy and healthcare management. Existing EMA approaches are limited because: (1) They depend on pre-selected tests and conditions that are not optimized to the patient's behavioral or functional level or to changes in the patient's behavior or function during treatment. Consequently, patients perform the same test each time, many test items may be redundant, and the dynamic range of each patient's performance may be sampled inefficiently. (2) The testing schedule is pre-determined and does not update in response to changes or patterns detected in the data. Consequently, conservative testing schedules are selected, which may place unnecessary burden on patients in order to sample as much data as the patient can sustain and this may reduce the quality of data.

SUMMARY OF THE INVENTION

The disclosed methods and systems address the foregoing problems and can have the precision of clinical and research grade apparatuses while, for example, operating on mobile testing equipment. One example embodiment of the invention is a method of determining an optimal schedule for obtaining assessments of a physical subject. According to the example method, a set of assessments of a measurable biological or behavioral quantity of the physical subject is obtained from a data source over a particular time period and stored in memory. A processor in communication with the memory determines a first estimate of values of the measurable quantity of the physical subject over the particular time period based on the set of assessments, and stores the first estimate of values in the memory. For each time point during the particular time period that it is possible to obtain an assessment of the physical subject, the processor determines a maximum likelihood estimate for the measurable quantity at that time point, and stores the set of maximum likelihood estimates in the memory. The processor determines a second estimate of values of the measurable quantity of the physical subject over the particular time period based on the set of assessments and the set of maximum likelihood estimates, and stores the second estimate of values in the memory. The processor compares the first estimate of values with the second estimate of values as a function of time to obtain a set of divergences for the time points during the particular time period that it is possible to obtain an assessment of the physical subject, and stores the set of divergences in the memory. The processor determines at least one next time to obtain an assessment of the physical subject based on a maximum value of the set of divergences. When determining the first estimate of values and the second estimate of values, the processor may calculate a Gaussian Process Regression, and when obtaining the set of divergences, the processor may calculate a Kullback-Leibler Divergence.

The method can further include obtaining a subsequent assessment of the measurable biological or behavioral quantity of the physical subject at the determined at least one next time, adding the subsequent assessment to the set of assessments in the memory, and repeating the determinations of the estimates of values, maximum likelihood estimates, divergences, and at least one next time to obtain an assessment of the physical subject.

In some embodiments, the particular time period is based on knowledge of the physical subject, and the set of assessments of the physical subject are distributed over the particular time period based on knowledge of the physical subject. In some embodiments, the data source is an existing data set including information about the physical subject, and obtaining the set of assessments includes mining the set of assessments from the existing data set.

In many embodiments, the data source can include a sensor in communication with the physical subject and can be configured to measure the biological or behavioral quantity of the physical subject, or the method can include transmitting the determined next time to testing equipment in communication with the physical subject or causing testing equipment to obtain a subsequent assessment of the measurable biological or behavioral quantity of the physical subject at the determined at least one next time.

Another example embodiment of the invention is a system for determining an optimal schedule for obtaining assessments of a physical subject. The system includes memory, a data source, a hardware processor in communication with the memory and the data source, and a control module in communication with the processor. The hardware processor performs a predefined set of operations in response to receiving a corresponding instruction selected from a predefined native instruction set of codes. The control module includes (i) a first set of machine codes selected from the native instruction set for causing the hardware processor to obtain, from the data source, over a particular time period and store, in the memory, a set of measurable biological or behavioral quantity assessments of the physical subject, (ii) a second set of machine codes selected from the native instruction set for causing the hardware processor to determine and store, in the memory, a first estimate of values of the measurable quantity of the physical subject over the particular time period based on the set of assessments, (iii) a third set of machine codes selected from the native instruction set for causing the hardware processor, for each time point during the particular time period that it is possible to obtain an assessment of the physical subject, to determine and store, in the memory, a maximum likelihood estimate for the measurable quantity at that time point, resulting in a set of maximum likelihood estimates, (iv) a fourth set of machine codes selected from the native instruction set for causing the hardware processor to determine and store, in the memory, a second estimate of values of the measurable quantity of the physical subject over the particular time period based on the set of assessments and the set of maximum likelihood estimates, (v) a fifth set of machine codes selected from the native instruction set for causing the hardware processor to compare the first estimate of values with the second estimate of values as a function of time to obtain and store, in the memory, a set of divergences for the time points during the particular time period that it is possible to obtain an assessment of the physical subject, and (vi) a sixth set of machine codes selected from the native instruction set for causing the hardware processor to determine and store, in the memory, at least one next time to obtain an assessment of the physical subject based on a maximum value of the set of divergences.

In many embodiments, the control module includes (i) a seventh set of machine codes selected from the native instruction set for causing the hardware processor to obtain a subsequent assessment of the measurable biological or behavioral quantity of the physical subject at the determined at least one next time, (ii) an eighth set of machine codes selected from the native instruction set for causing the hardware processor to add the subsequent assessment to the set of assessments in the memory, and (iii) a ninth set of machine codes selected from the native instruction set for causing the hardware processor to re-execute the second, third, fourth, fifth, and sixth set of machine codes.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

Figure 1:
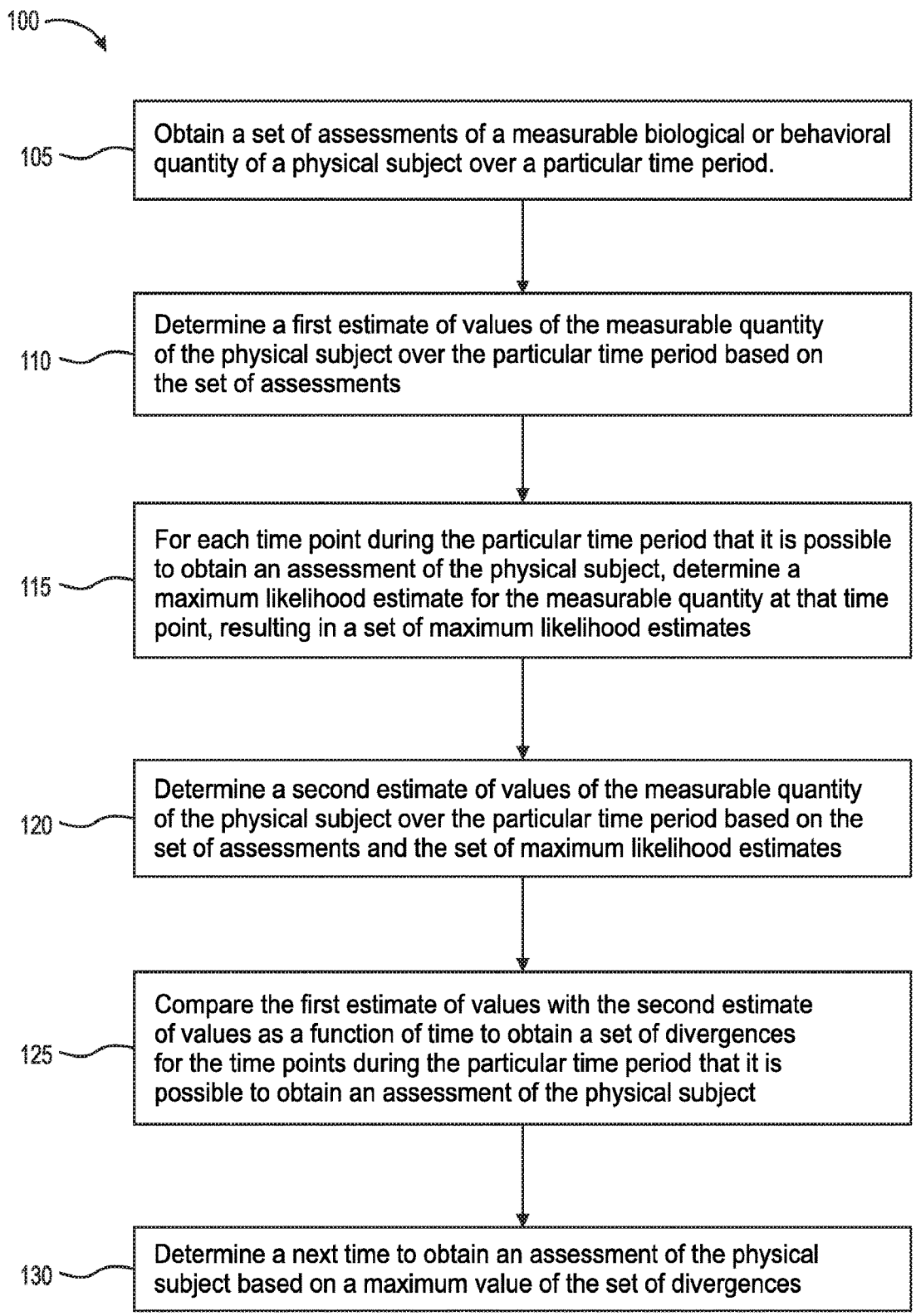
FIG. 1 is a flow chart illustrating determining an optimal schedule for obtaining assessments of a physical subject, according to an example embodiment of the present invention.

A description of example embodiments of the invention follows.

The disclosed methods and systems provide adaptive test administration with respect to a physical subject. The disclosed methods and systems can be used to efficiently collect clinical assessment data from a patient, for example, can use machine learning approaches to detect unknown patterns in the assessment data, and can modify a testing schedule in real-time based on the analyses. The disclosed techniques can be used to (1) control the timing of each assessment in order to collect data at times and under conditions that are most informative about, for example, the health status of patient, and (2) modify the content of a test/intervention to optimally sample data at the most informative levels with respect to, for example, an individual patient. Such optimized testing schedules can be informed by known prior information about the time course of functional variation, which may occur over seconds (e.g., between blinks in the context of dry eye disease), daily (e.g., in diabetic retinopathy), or weeks (e.g., in optic neuritis in muscular sclerosis) or longer (e.g., in the aging eye). It should be appreciated that while the above provides example of timing in relation to the testing and treatment of eye diseases, the methods and systems can be applied to a variety of assessment situations, such as, for example, medical insurance, healthcare provision, personalized health and fitness tracking, and pharmaceutical applications, where they can be used for, e.g., individualized/personalized medicine, remote monitoring, and clinical trial management by determining optimal test schedules for detecting presence, progression, or remediation of disease, disease symptoms, and treatment side effects as well as the scheduling of therapeutic interventions and the possible cessation of treatment.

The disclosed adaptive methods and systems significantly reduce the frequency of data collection without loss in accuracy or precision and can even increase test reliability through reduction in redundancy and prevention of frustration and fatigue in a physical subject (e.g., a medical patient). Additionally, by detecting underlying patterns in the data, estimates of variability of each sample can be reduced. If these patterns are not accounted for, variability arising from fluctuations in the underlying unknown function is likely attributed to measurement error and behavioral noise, which can lead to significant increases in the sample sizes required to power a research study. The disclosed approach, therefore, leads to significant reductions in the size and cost of clinical trials as well as the detection of informative patterns of symptom change.

The disclosed methods and systems include direct applications of an optimal sampling technique to clinical assessment, and allow for accurate estimates of the variance of an unknown function at a single time step (i.e., measurement noise) independently of the variance due to fluctuations in the function over time by, for example, using an information theoretic approach to determining an optimal subsequent time point at which to acquire a next assessment.

Some example advantages of the disclosed methods and systems include the ability to estimate an unknown, underlying function using a small number of free parameters that remain constant regardless of the number of data points being estimated; thus, substantially reducing the error of the function estimate. Because estimates of the measurement error are achieved with a minimum of sampled assessments, and with great accuracy, the statistical power of clinical trials can be greatly increased. The disclosed methods and systems allow for accurate estimates of complex, irregular functions without the need for fitting a large number of local smoothing parameters. Local smoothing can be achieved via Gaussian Process Regression (GPR), for example, using only generic assumptions about the covariance of the underlying function.

The disclosed methods and systems generate fast estimates of an unknown time-series function using a minimum number of observations in the form of, for example, clinical measurements. The unknown function is assumed to be periodic and an estimate of the time period of a single cycle of the function can be derived from prior information about the quantities being measured or deduced from first principles. The estimation process begins by obtaining a small number of clinical measurements at equal time intervals. Nine to eleven measurements, for example, can be adequate for a fast, accurate estimation of 100 time points.

GPR can be performed on the initial measurements, yielding an estimate of the unknown function for all time points in the period, the variance of the function estimate, and the measurement noise. The variance of the estimate can be used to derive the likelihood of the estimate across all time points, i.e., the probability of observing all possible values of the underlying function at a given time.

An optimal subsequent time point can be selected at which to acquire a subsequent measurement by examining each time point to be estimated in turn and making a hypothesis as to the value of a measurement acquired at that point. For each time point, the hypothesized value of an observation at that point can be the current estimate at that point. This is the maximum likelihood solution: the expectation over all possible values that could be observed at that time. GPR can then be performed again using the current measurements plus the additional hypothesized one yielding a new, hypothetical function estimate and its associated likelihood function. An information theoretic technique, the Kullback-Leibler Divergence, can be used to compare the likelihood of the current estimate to that of the hypothetical estimate. The time point at which the hypothetical likelihood differs most from that of the current estimate is chosen as the next time at which to acquire a measurement.

Using this technique, the underlying function can be sampled at time points where change in the function over time is maximal and, thus, gives a clinician the most information about the form of the underlying function, avoiding locations where the function is not changing and which, thus, offer little information to the clinician.

FIG. 1 is a flow chart 100 illustrating determining an optimal schedule for obtaining assessments of a physical subject, according to an example embodiment of the present invention. A set of assessments of a measurable biological or behavioral quantity of the physical subject is obtained (105) from a data source over a particular time period and stored in memory. A processor in communication with the memory determines (110) a first estimate of values of the measurable quantity of the physical subject over the particular time period based on the set of assessments, and stores the first estimate of values in the memory. For each time point during the particular time period that it is possible to obtain an assessment of the physical subject, the processor determines (115) a maximum likelihood estimate for the measurable quantity at that time point, and stores the set of maximum likelihood estimates in the memory. The processor determines (120) a second estimate of values of the measurable quantity of the physical subject over the particular time period based on the set of assessments and the set of maximum likelihood estimates, and stores the second estimate of values in the memory. The processor compares (125) the first estimate of values with the second estimate of values as a function of time to obtain a set of divergences for the time points during the particular time period that it is possible to obtain an assessment of the physical subject, and stores the set of divergences in the memory. The processor determines (130) at least one next time to obtain an assessment of the physical subject based on a maximum value of the set of divergences.

Figure 2:
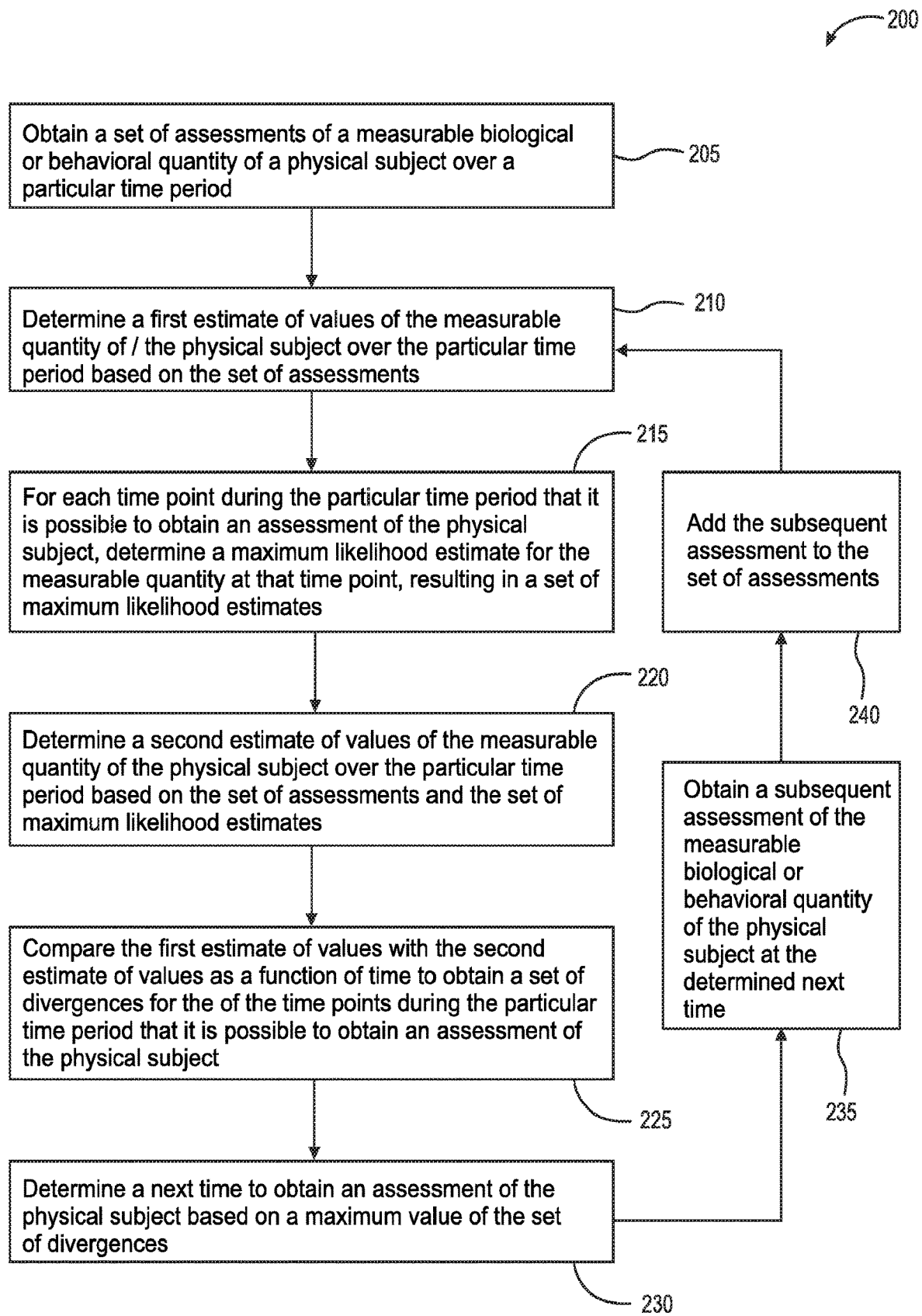
FIG. 2 is a flow chart illustrating determining an optimal schedule for obtaining assessments of a physical subject, according to an example embodiment of the present invention.

FIG. 2 is a flow chart 200 illustrating determining an optimal schedule for obtaining assessments of a physical subject, according to an example embodiment of the present invention. The illustrated method is similar to that of FIG. 1 (e.g., 205-230), but further illustrates obtaining (235) a subsequent assessment of the measurable biological or behavioral quantity of the physical subject at the determined at least one next time and adding (240) the subsequent assessment to the set of assessments in the memory. FIG. 2 illustrates the determinations (205-230) of the estimates of values, maximum likelihood estimates, divergences, and at least one next time to obtain an assessment of the physical subject can be repeated for an arbitrary number of iterations.

Figure 3:
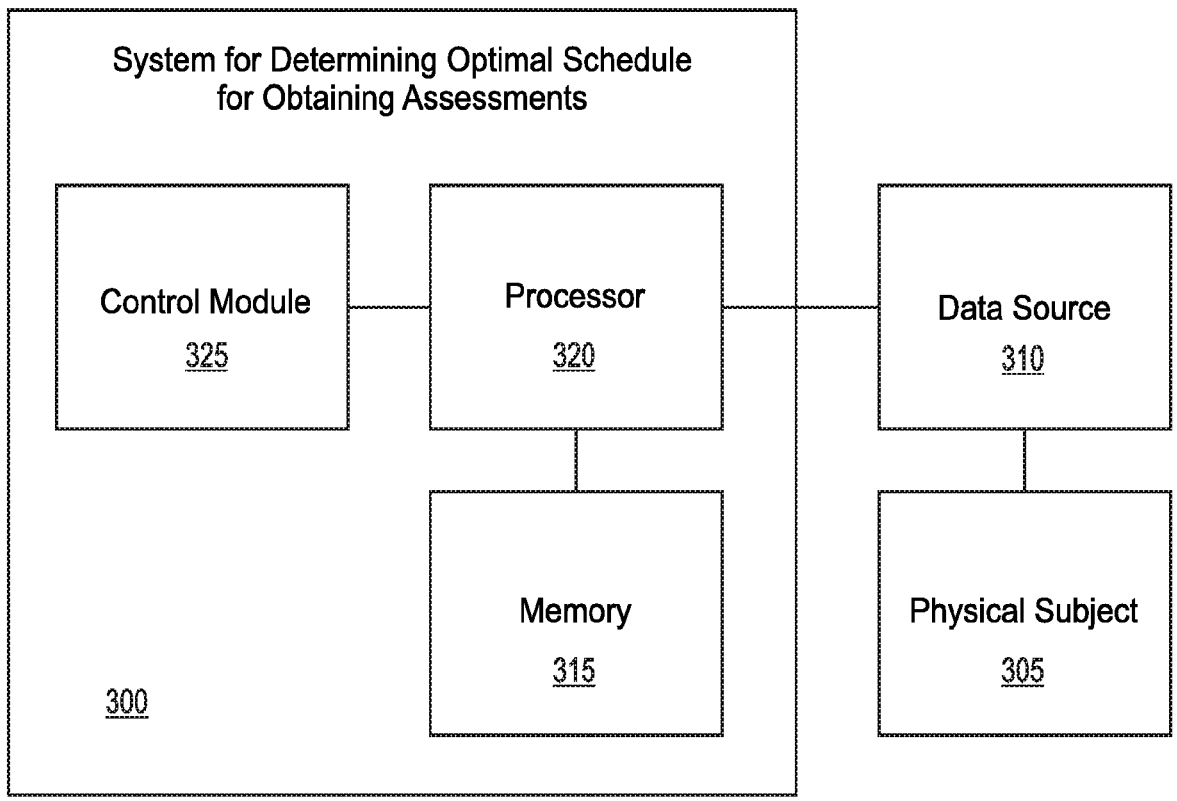
FIG. 3 is a block diagram illustrating a system for determining an optimal schedule for obtaining assessments of a physical subject, according to an example embodiment of the present invention.

FIG. 3 is a block diagram illustrating a system 300 for determining an optimal schedule for obtaining assessments of a physical subject 305, according to an example embodiment of the present invention. The system 300 includes memory 315, a data source 310, a hardware processor 320 in communication with the memory 315 and the data source 310, and a control module 325 in communication with the processor 320. The control module 325 is configured to cause the hardware processor 320 to (i) obtain, from the data source 310, over a particular time period and store, in the memory 315, a set of measurable biological or behavioral quantity assessments of the physical subject 305, (ii) determine and store, in the memory 315, a first estimate of values of the measurable quantity of the physical subject 305 over the particular time period based on the set of assessments, (iii) for each time point during the particular time period that it is possible to obtain an assessment of the physical subject 305, determine and store, in the memory 315, a maximum likelihood estimate for the measurable quantity at that time point, resulting in a set of maximum likelihood estimates, (iv) determine and store, in the memory 315, a second estimate of values of the measurable quantity of the physical subject 305 over the particular time period based on the set of assessments and the set of maximum likelihood estimates, (v) compare the first estimate of values with the second estimate of values as a function of time to obtain and store, in the memory 315, a set of divergences for the time points during the particular time period that it is possible to obtain an assessment of the physical subject 305, and (vi) determine and store, in the memory 315, at least one next time to obtain an assessment of the physical subject 305 based on a maximum value of the set of divergences.

Figure 4:
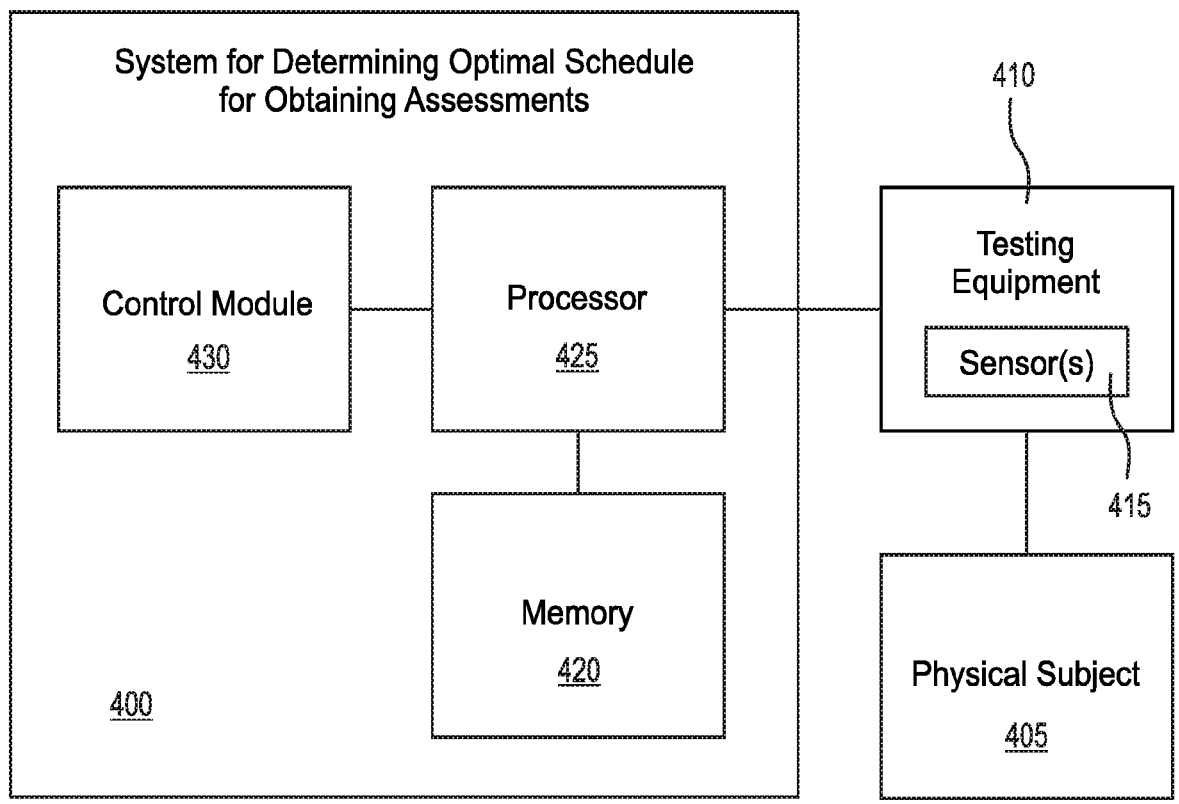
FIG. 4 is a block diagram illustrating a system for determining an optimal schedule for obtaining assessments of a physical subject, according to an example embodiment of the present invention.

FIG. 4 is a block diagram illustrating a system 400 for determining an optimal schedule for obtaining assessments of a physical subject 405, according to an example embodiment of the present invention. The illustrated system 400 is similar to that of FIG. 3 and includes memory 420, a data source, a hardware processor 425 in communication with the memory 420 and the data source, and a control module 430 in communication with the processor 425, but shows that the data source can include sensor(s) 415 in communication with the physical subject 405 to measure the biological or behavioral quantity of the physical subject 405, and that the processor 425 can transmit the determined next time to testing equipment 410 in communication with the physical subject 405 or cause the testing equipment 410 to obtain a subsequent assessment of the measurable biological or behavioral quantity of the physical subject 405 at the determined at least one next time.

Embodiments of the present invention utilize an analytical technique applied to time series data. The disclosed methods and systems generate a minimum-error estimate of the unknown, underlying time series function while simultaneously minimizing the number of samples required to optimize the estimate. The methods and systems operate either in real time or by mining an existing data set. Real-time estimates can be generated for functions that are known to be cyclical and for which the number of subsequent cycles available for sampling is unrestricted. Following each sample, the methods/systems generate a function estimate and then choose a next best time at which to acquire a sample. When an existing data set is used, estimates can be generated for any function with data defined over any finite time interval. When using an existing data set, the methods/systems generate an optimized sampling schedule that can then be used to sample from a new data source in real time.

The methods and systems can also generate simultaneous estimates of multiple time series functions defined over the same time span. A single optimized sampling schedule is derived which can be used for simultaneous sampling of each function. The methods and systems can also generate schedules for sampling at multiple successive time points. For example, if there is a limited number of, say, n samples that can be taken, the methods and systems determine the optimal subsequent n time points at which to obtain samples.

General Description

According to example embodiments of the invention, methods and systems take successive samples from an underlying function and, following each sample, generate an estimate of the function using, for example, Gaussian Process Regression (GPR). The optimal time at which to next sample the function is derived by comparing the current estimate of the function to hypothetical estimates made at future times. The maximum likelihood predicted value of a sample taken at a given time is the current GPR estimate for that time. This predicted sample is added to the current set of actual samples and a new, hypothetical GPR estimate is derived. The hypothetical estimate is compared to the current estimate by, for example, determining their Kullback-Leibler divergence (KLD). The time point at which the KLD is maximized is selected as the next time at which to obtain a sample. The time of maximum divergence is the time brings about the greatest change in the estimate of the underlying function and which thus yields the most information regarding its form.

Let $F_i(t)$ equal one of i unknown time series functions to be estimated defined over a finite time span, $T=\{t_0, \ldots, t_N\}$. Let $y_i(t)$ equal an observation of the function made at time, t, corrupted by normally distributed noise with standard deviation, $\sigma_{y,i}$:

$$y_i(t) = F_i(t) + \varepsilon$$

$$\varepsilon \sim N(0, \sigma_{y,i})$$

The example methods and systems return an estimate, $G_i(t)$, of $F_i(t)$ and an estimate, $\hat{\sigma}_{y,i}$, of $\sigma_{y,i}$. It also returns a schedule of successive times from T that optimize the estimates with the minimum number of observations.

The following describes steps involved in calculating the function estimates. These steps are carried out independently for each $F_i(t)$ and so the subscript, i, is omitted for notational simplicity.

Form Prior Distribution Over Noise Estimates

To derive $\hat{\sigma}_y$, first form a prior distribution over $\sigma_y$. Assume that the maximum possible value of $\sigma_y$ equals the standard deviation, $\sigma$, of F(t) measured over the timespan, T, and make a reasonable estimate, $\hat{\sigma}$, of it from existing data. Assume the prior distribution over $\sigma_y$ to be normally distributed and set its initial value over a range of possible values, $\hat{\sigma}_y$. The log prior is given by:

$$P(\sigma_y = x) = \ln\left(\frac{1}{\sqrt{2\pi}\,\sigma_{prior}}\right) - \frac{(x - \mu_{prior})^2}{2\sigma_{prior}^2}$$

$x = \{0, \ldots, \hat{\sigma}\}$ $\mu_{prior} = \hat{\sigma}/2$ $\sigma_{prior} = \hat{\sigma}/12$ The prior distribution implicitly assumes that extreme values of $\sigma_y$ are unlikely. Low values of $\sigma_y$ imply that most observed variability comes from the underlying function, which has low covariance between the values at different time points. High values of $\sigma_y$ imply that the function has high covariance, e.g., it's a line with slope near zero, and most observed variability arises from measurement error. The initial prior distribution assumes that the true value lies somewhere between the extremes.

Acquire Initial Samples

The example methods and systems begin by obtaining a small number of samples from F(t) at a set of equally-spaced time intervals. Let $Y = \{y_{t_0}, \ldots, y_{t_N}\}$ equal the set of all samples from F(t) where each $y_t$ is the set of all observations made at time, t. Let t be the set containing each unique time from Y that contains one or more samples. Since all functions are sampled at the same times, t is identical for all $F_i(t)$. The initial sample times, $t = \{0, \tau, 2\tau, \ldots, (N-1)\tau, N\tau\}$, are selected with the time interval, $\tau$, chosen to divide the time interval of interest (e.g., the estimated length of a cycle or, in the case in which an existing data set is used, the interval over which F(t) is sampled) into equal parts.

Derive the Covariance Kernel

GPR assumes that F(t) is drawn from a 0-mean, N-dimensional normal distribution of functions such that:

$$F(t) \sim N(0_N, \Sigma)$$

where $0_N$ is a zero vector of length N, and $\Sigma$ is the N×N matrix giving the variance and covariance of observations made at each time point. The initial samples are used to derive a model of $\Sigma$ (defined at the currently sampled time points in t) in the form of the covariance kernel, K. The kernel takes the form of a squared-exponential function augmented by the current estimate of the additive noise, $\hat{\sigma}_y$:

$$K(t,t) = \alpha e^{\frac{-X(t,t)^2}{2\beta^2}} + \hat{\sigma}_y^2 I$$

where X(t,t) is the distance between the current sampled time points:

$$X(t,t) = \begin{bmatrix} t_0 - t_0 & t_1 - t_0 & \dots & t_{N_s} - t_0 \\ t_0 - t_0 & t_1 - t_0 & \dots & t_{N_s} - t_1 \\ \vdots & \vdots & \ddots & \vdots \\ t_0 - t_{N_s} & t_1 - t_{N_s} & \dots & t_{N_s} - t_{N_s} \end{bmatrix}$$

$N_s$ is the number of current samples, and I is the identity matrix.

Derive the maximum a posteriori estimate of additive noise, $\hat{\sigma}_y$, by first iterating over each of its possible values in x (effectively treating it as a constant) and then fitting $\alpha$ (the variance) and $\beta$ (the covariance 'bandwidth') by maximum likelihood for each iteration. The log-likelihood of the current samples given the kernel parameters is given by:

$$L(s \mid \alpha, \beta, \sigma_y = x) = -\frac{1}{2}(s^T K^{-1} s + \ln(|K|) + \ln(2\pi) N_S)$$

$$K(t,t) = \alpha e^{\frac{-X(t,t)^2}{2\beta^2}} + x^2 I$$

where s is an $N_s \times 1$ vector containing all current sampled values in Y, and | . . . | indicates the determinant. Next, calculate the log posterior probability of each noise estimate given the samples and the corresponding best fitting parameter values, $\alpha$ and $\beta$:

$$P(\sigma_y = x \mid s, \alpha, \beta) = L(s \mid \alpha, \beta, \sigma_y = x) + P(\sigma_y = x)$$

The current noise estimate is given by:

$$\hat{\sigma}_y = \text{argmax}_x P(\sigma_y = x \mid s, \alpha, \beta)$$

Derive the Regression Estimate

Next a GPR estimate is determined for F(t). For each time point of interest, $t_n$ (n={0, . . . , N}), calculate the distance, $x_*$, of $t_n$ from all currently sampled time points in t:

$$x_* = \{t_0 - t_n, \dots, t_{N_s} - t_n\}$$

and derive the estimated covariance, $k_*$, given the current parameter estimates, $\alpha$ and $\beta$:

$$k_*(t) = \alpha e^{\frac{-x_*^2}{2\beta^2}}$$

The GPR estimate, $G(t_n)$, of $F(t_n)$ is then:

$$G(t_n) = k_* K^{-1} s$$

and the variance of the estimate is given by:

$$v_{t_n} = \alpha + \hat{\sigma}_y^2 - k_* K^{-1} k_*^T$$

The full function estimate, G(t), is derived by iterating over each time point, n, in the range.

Determine the Optimal Next Sample Time

Next determine the optimal time or set of times, $t_{opt}$, at which to get the next samples. Let $T_* = \{t_0, \dots, t_C\}$, for $$C = \binom{N}{k},$$

equal the set of all groups of time points to be considered for sampling. When only a single sample time is needed, k=1, and $T_* = [1, 2, \dots, N]$. Under some circumstances, it may be desirable to determine multiple times at which to get samples. When, for example, there is a limit on the number of samples that can be taken, set k equal to the total number of possible samples and then determine the set of k optimal sampling times. Having collected a new sample at the first time in the sequence, a new schedule of size k−1 can be derived, and so forth. When it is desirable to determine the two best times at which to obtain samples during the time span, N, for example, k=2, and T=[(1 2), (1 3), . . . , (1 N), (2 3), . . . (N−1 N)].

Iteratively select each set of time points $t_c$ (for c= {0, . . . , C}) in $T_*$ and derive the set, $\hat{y}_i(t_c)$, of maximum likelihood estimates of sample values from $F_i(t_c)$. The maximum likelihood sample values are simply the current GPR estimates at those times:

$$\hat{y}_i(t_c) = G_i(t_c)$$

The values in $\hat{y}_i(t_c)$ are added to the set of current samples. Let $\hat{s}_i$ equal the $(N_s+k) \times 1$ vector giving the aggregate of current samples, $s_i$, from $F_i(t)$, and the hypothetical samples in $\hat{y}_i(t_c)$. If, in $s_i$, there is already a sample at any of the time points in $t_c$, the arithmetic mean of the samples is taken. Then a new, hypothetical GPR estimate, $\hat{G}_i(t)$, is derived as above, but replacing $s_i$ with $\hat{s}_i$.

Let $\xi(y_i|G_i(t), v_{t,i})$ equal the likelihood of the current GPR estimate at time t:

$$\xi(y_i \mid G_i(t), v_{t,i}) = \frac{1}{\sqrt{2\pi v_{t,i}}} e^{\frac{-(y_i - G_i(t))^2}{2v_{t,i}}}$$

where y is a m×1 vector with values defined over some finite interval in the range of $F_i(t)$. And let $\xi(y_i|\hat{G}_i(t), \hat{v}_{t,i})$ be the similar likelihood function for $\hat{G}_i(t)$.

Calculate the Kullback-Leibler divergence of the current and the hypothetical GPR estimates:

$$D_{i,t_c} = \sum_n \sum_m \xi(y_{i,m} \mid G_i(t_n), v_{t_n,i}) \ln\left(\frac{\xi(y_{i,m} \mid G_i(t_n), v_{t_n,i})}{\xi(y_{i,m} \mid \hat{G}_i(t_n), \hat{v}_{t_n,i})}\right)$$

The optimal times at which to get the next samples are given by:

$$t_{opt} = \text{argmax}_{t_c} \Sigma_i D_{i,t_c}$$

Acquire the Next Sample

The next iteration begins by getting a sample at $t_{opt}$, adding the sample to Y, and repeating the process.

Update the Noise Prior

Each time a new sample is acquired and the covariance kernel, K, is recalculated, the noise prior, $P(\sigma_y = x)$, is updated by replacing it with the posterior, $P(\sigma_y = x \mid s, \alpha, \beta)$.

Getting the Optimal Sampling Schedule Using Existing Data

The above describes the process for sampling and generating function estimates in real time. When existing data sets are used, example methods and systems can calculate the residual error of the function estimate made on each step with regards to the entire data set. The optimal number of samples is that corresponding to the function estimate at which the error approaches a low asymptote. Sample times may be chosen in staggered order. The optimal schedule consists of the selected times arranged in temporal order.

Example Iterations

The following is a step-by-step illustration of an example method of determining an optimal schedule for obtaining assessments of a physical subject, with reference to FIGS. 5-11.

Figure 5:
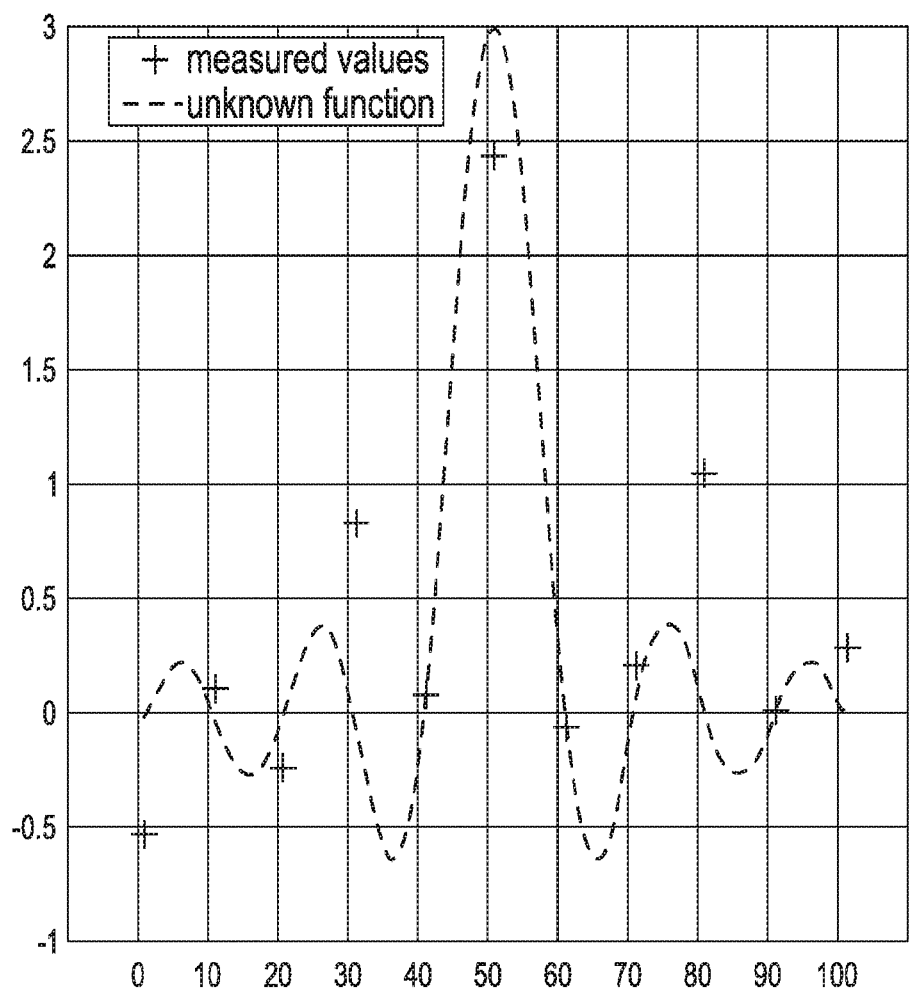
FIG. 5 is a graph illustrating assessments of a physical subject taken over a particular time period and an unknown function associated with those assessments.

(1) Measurements from the unknown function are taken at regular intervals over the time span of interest. As shown in FIG. 5, eleven measurements, shown by crosses, are taken at ten-minute intervals from t={1, . . . , 101}.

Figure 6:
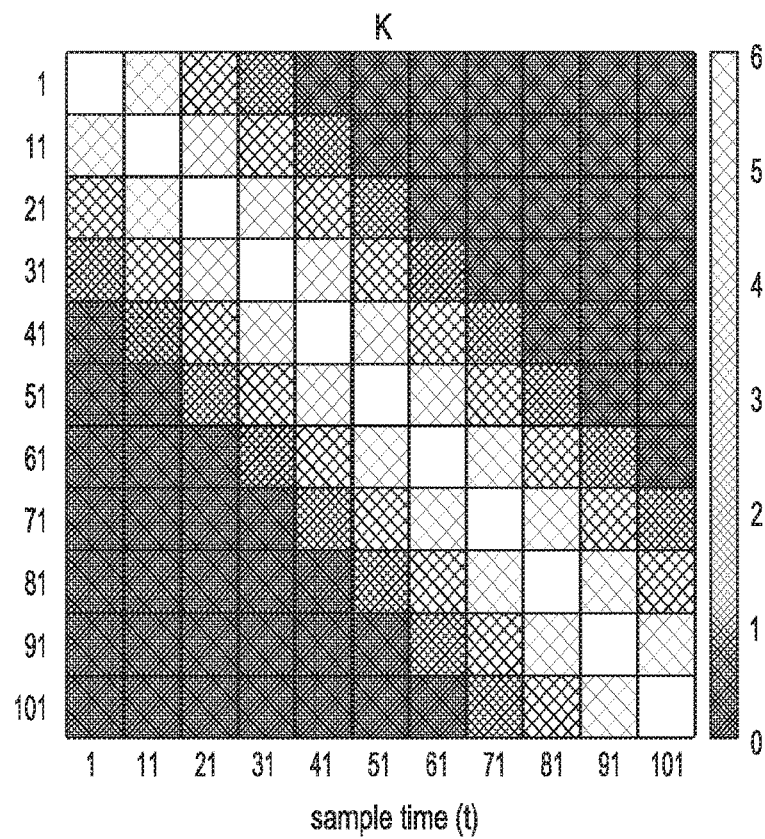
FIG. 6 is matrix illustrating covariances of the assessments of a physical subject.

(2) A model of the variance and covariance of the measurements is derived in the form of the kernel, K, given by:

$$K(t, t) = \alpha e^{\frac{-X(t,t)^2}{2\beta^2}} + \hat{\sigma}_y^2 I$$

where $X(t, t)$ is a matrix containing the distances between the measured time points and $\alpha$, $\beta$, and $\hat{\sigma}_y$ are parameters fit to the data by maximum likelihood. The resulting matrix, K, is shown in FIG. 6. The parameter values have been scaled to facilitate visualization of the covariances.

Figure 7:
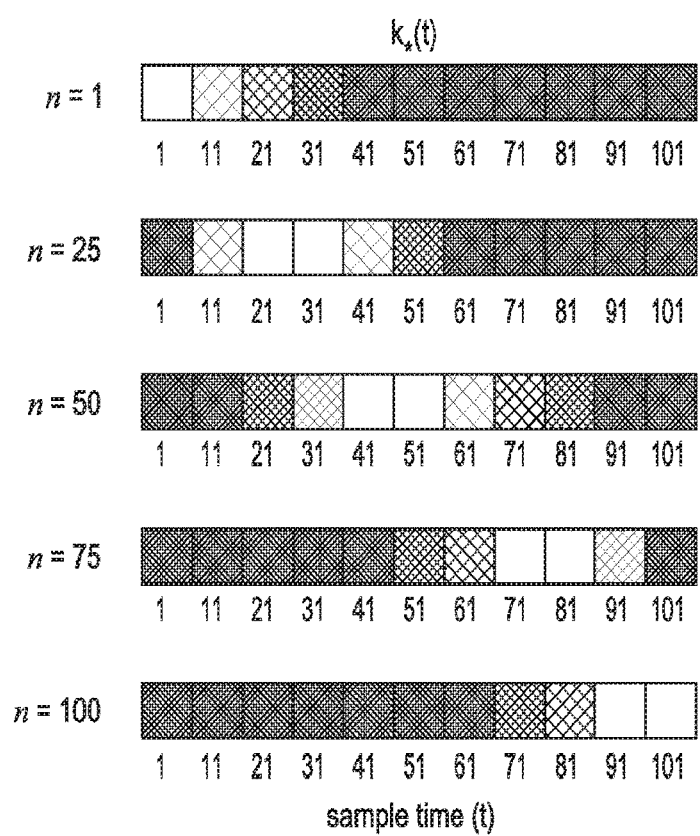
FIG. 7 is a subset of a matrix illustrating covariances of the assessments of a physical subject.

(3) Next, calculate an estimate of the unknown function from the initial measurements, resulting in estimated values for every time point, $t_n$, for n={1, 2, . . . , 100, 101}. To do so, first estimate the covariance of the measurements at each time point, $t_n$, with respect to the initial measurements using the parameters $\alpha$, and $\beta$ derived in the previous step. The resulting row vector of estimated covariances is given by:

$$k_*(t) = \alpha e^{\frac{-x_*^2}{2\beta^2}},$$

where $x_*$ is a row vector giving the distance between the time point, $t_n$, and each of the current measurement times. A subset of the resulting vectors is shown in FIG. 7 (again, the covariances are scaled for display purposes).

Figure 8:
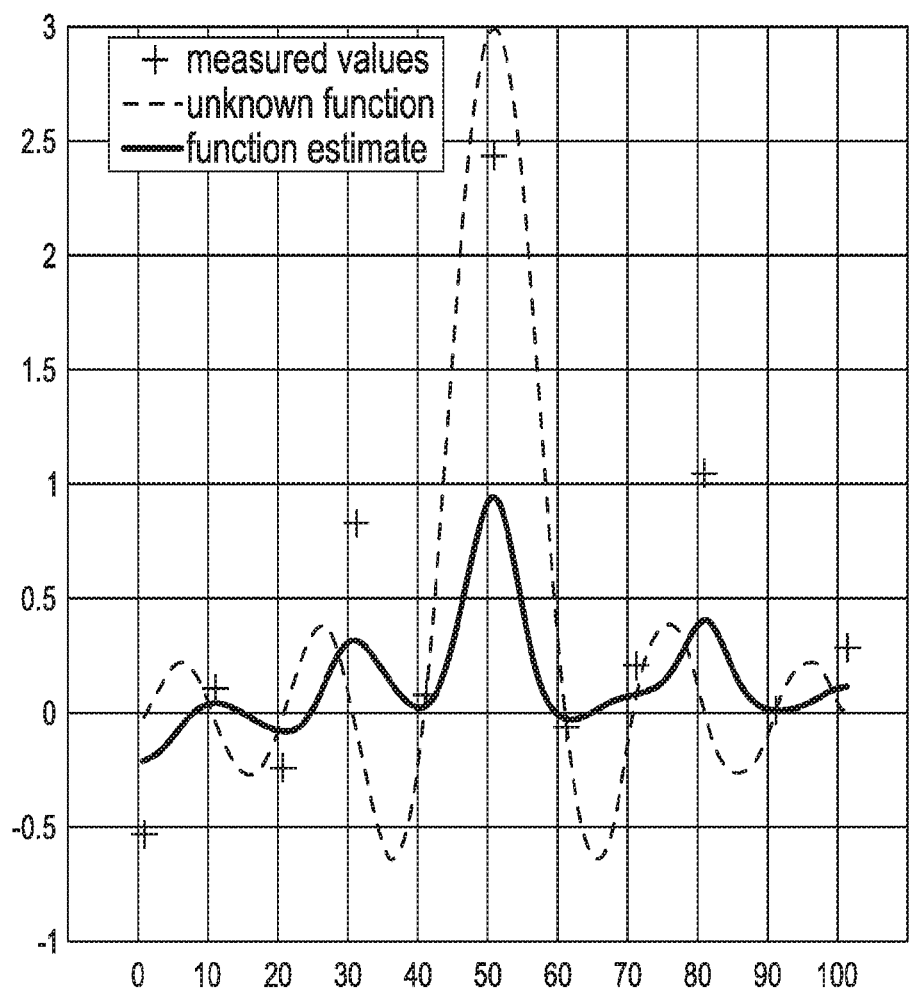
FIG. 8 is a graph illustrating an estimate of the unknown function of FIG. 5.

(4) The estimate of the unknown function for each time point, $t_n$, is given by:

$$\mathcal{G}_{(t_n)} = k_* K^{-1} s$$

where s is a column vector containing the current set of measurements. The full estimate across all time points, $\mathcal{G}(t)$, derived from the initial measurements, is shown in FIG. 8.

Figure 9:
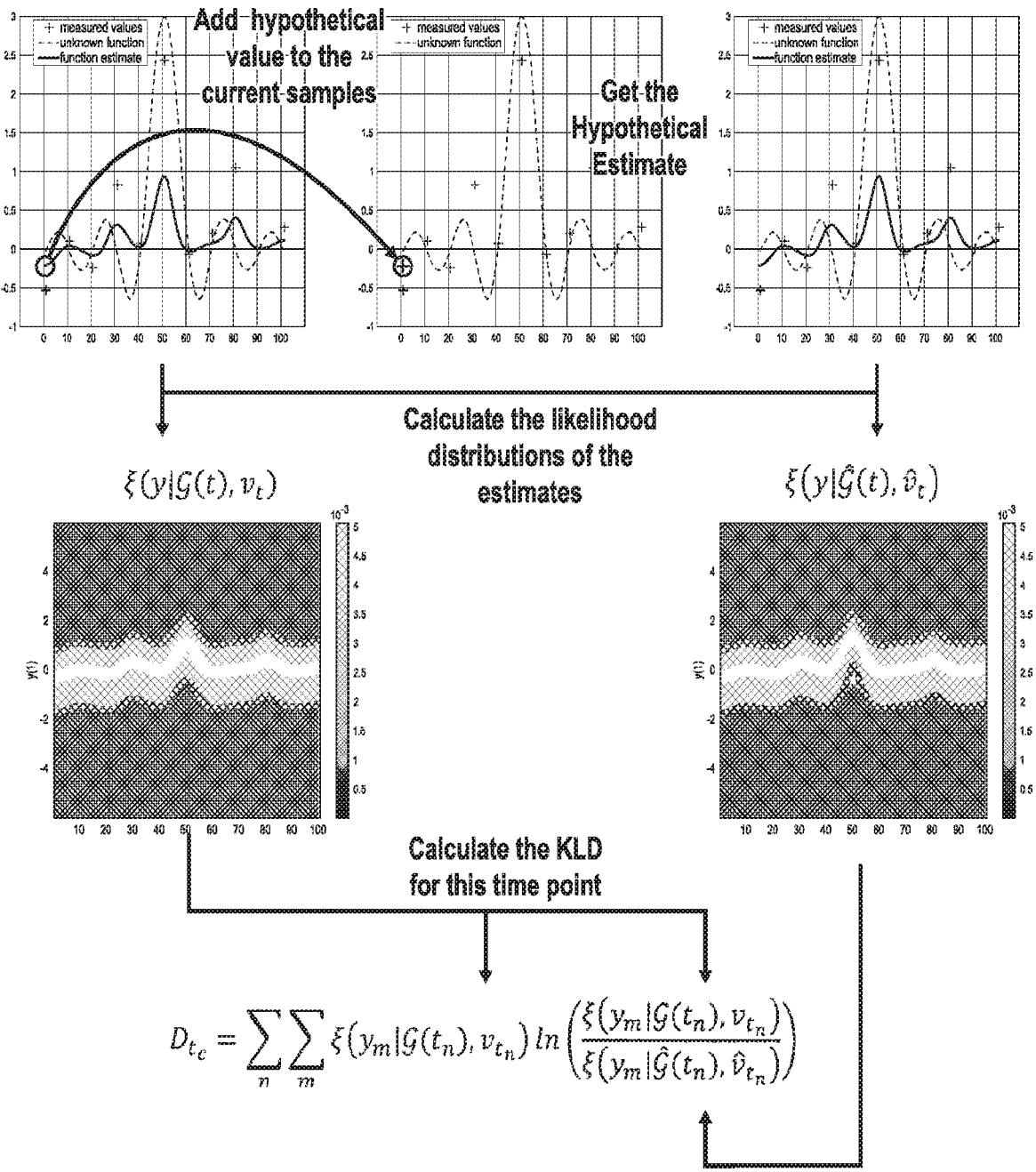
FIG. 9 is a flow chart with graphs illustrating calculating a likelihood of the estimated function of FIG. 8 and calculating a divergence of the estimated function and a hypothetical function.

(5) Next, derive the next optimal time at which to get a measurement, as shown in FIG. 9. First consider each possible time at which a measurement can be taken. These hypothetical measurement times may be denoted $t_c$ for c={1, 2 . . . , 100, 101}. For each time, estimate the value of an observation made at that time. This estimated value can be the value of the current function estimate at that time, $\mathcal{G}(t_c)$. The value $\mathcal{G}(t_c)$ is added to the current samples and a new, hypothetical function estimate is derived using the actual samples and the added hypothetical sample.

Calculate the likelihood of the current estimate, $\mathcal{G}(t)$, as a function of t across a range of possible values of y(t):

$$\xi(y \mid \mathcal{G}(t), v_t) = \frac{1}{\sqrt{2\pi v_t}} e^{\frac{-(y_i - \mathcal{G}(t))^2}{2v_t}}$$

where y is a m×1 vector with values defined over some finite interval in the range of F(t), and $v_t$ is the variance of the estimate at time, t. Similarly derive the likelihood function of the hypothetical estimate: $\xi(y \mid \hat{\mathcal{G}}(t), \hat{v}_t)$.

The likelihood distributions are used to calculate the Kullback-Leibler divergence, $D_{t_c}$, of the current of the current and hypothetical estimates:

$$D_{t_c} = \sum_n \sum_m \xi(y_m \mid \mathcal{G}(t_n), v_{t_n}) \ln\left(\frac{\xi(y_m \mid \mathcal{G}(t_n), v_{t_n})}{\xi(y_m \mid \hat{\mathcal{G}}(t_n), \hat{v}_{t_n})}\right)$$

This process is illustrated in FIG. 9.

Figure 10:
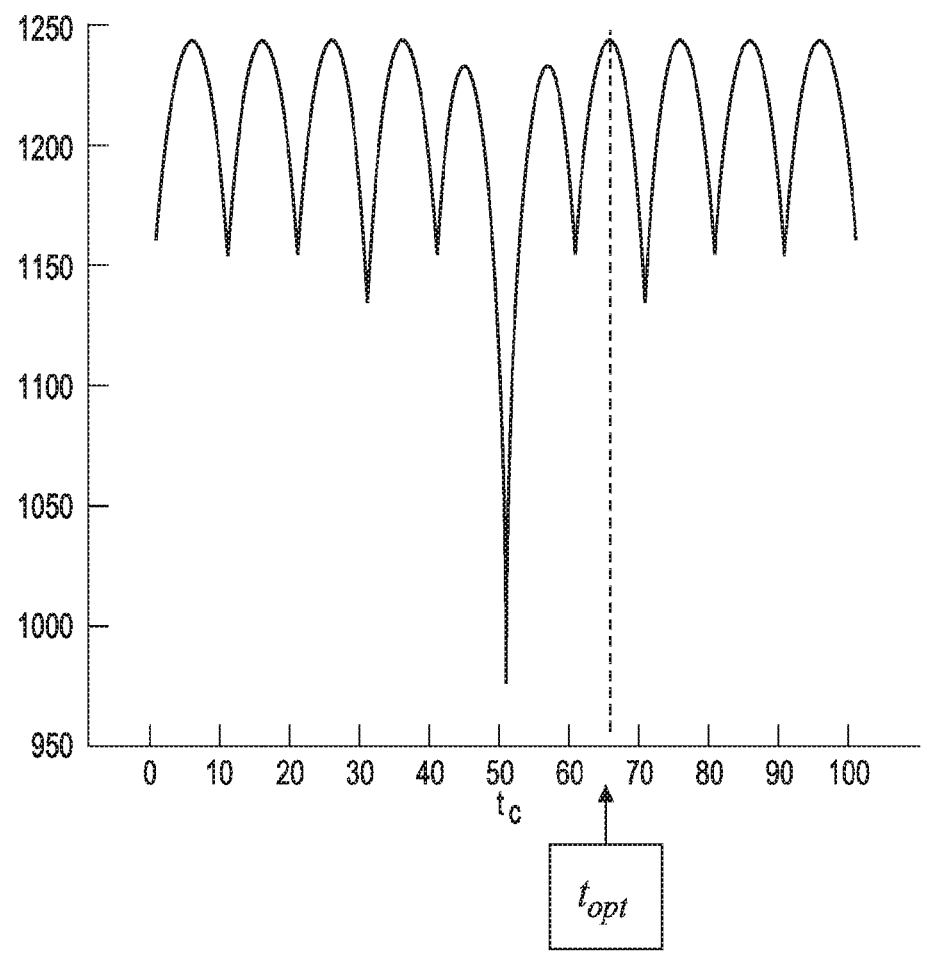
FIG. 10 is a graph illustrating the calculated divergence of FIG. 9 and a selection of an optimal time to obtain a next assessment.

The process can be repeated, calculating the KLD for all time points, $t_c$. The optimal time at which to get the next measurement is the time at which the KLD is maximized. In this example, the maximum value is at $t_c$=66, as shown in FIG. 10.

Figure 11:
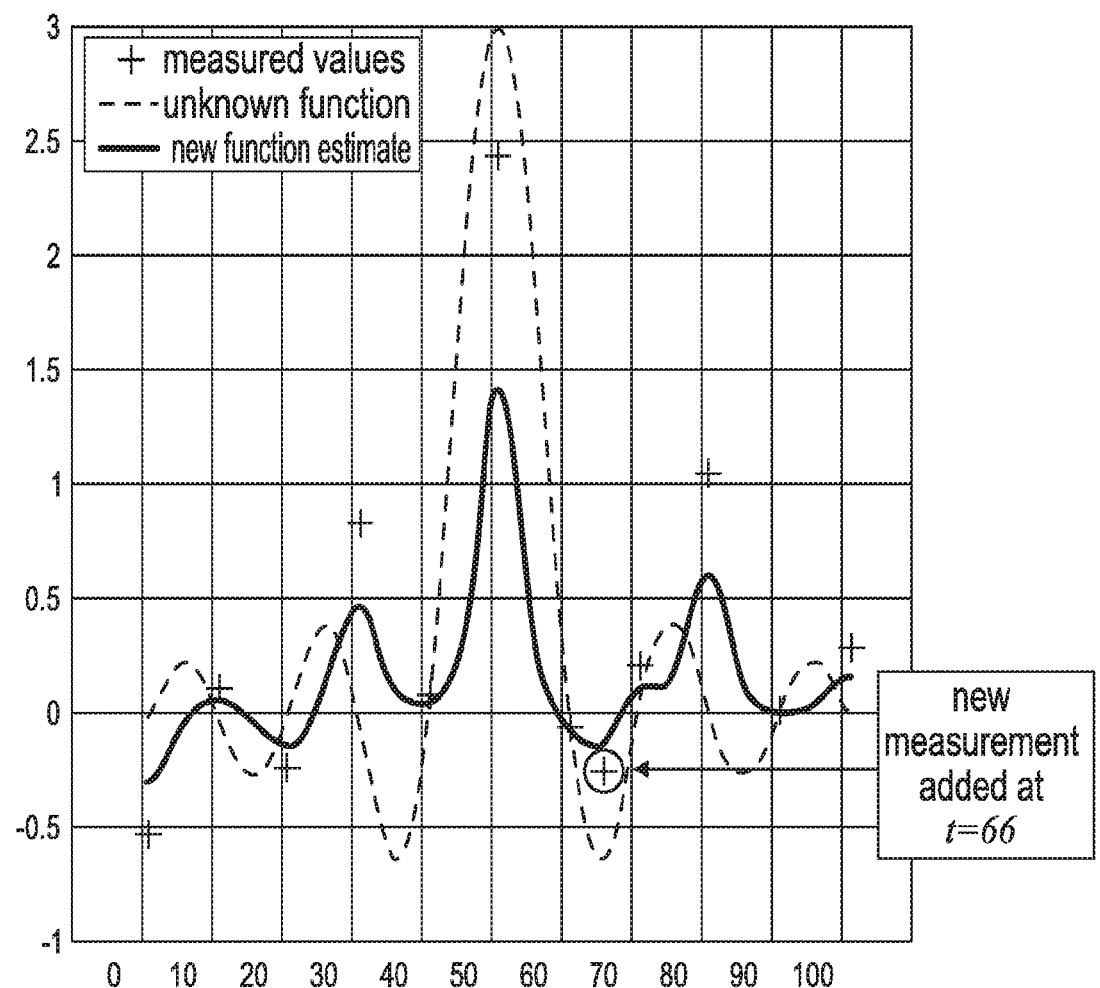
FIG. 11 is a graph illustrating an obtained next assessment added to the set of assessments.

(6) Next, obtain a measurement at $t = t_{opt} = 66$ and repeat the process from step 2. The new measurement and updated function estimate (from step 4), are shown in FIG. 11.

Example Applications of Methods and Systems

The following are three example applications of example embodiments of the invention. In each case, estimates of an unknown function and an optimized sampling schedule are determined. The first example (FIGS. 12A-C) is a simulation that provides ground-truth for demonstrating the ability of the methods and systems to fit an unknown function. The second (FIGS. 13A-C) is an example application to blood pressure (BP) measurement that demonstrates the ability of the methods and systems to fit multiple functions (i.e., systolic and diastolic BP) simultaneously. The third (FIGS. 14A-C) is an example application to measurement of the effects of drug treatment for macular degeneration. It demonstrates the ability of the methods and systems to mine a large longitudinal set of data from multiple subjects in order to derive an optimal schedule for assessing the effect of treatment.

Example 1—Simulation

The example application of Example 1 determines estimates of an underlying cyclical time series function of the form:

$$y(t) = \alpha \, \text{sinc}(2\pi t/N)$$

$$t = \{0, 1, \ldots, N\}$$

where N is the length of one cycle of y(t). The underlying function is unknown. Noisy samples, s(t), are obtained from the function where the samples are normally distributed with SD, $\sigma$:

$$s(t) \sim \mathcal{N}(y(t), \sigma)$$

Samples are obtained from multiple, successive cycles of the function, but for simplicity, all samples are depicted within a single cycle. So that, for example, if a sample at t=50 is selected followed by a sample at t=30, it is understood that the latter sample occurs in the subsequent cycle.

Figure 12A:
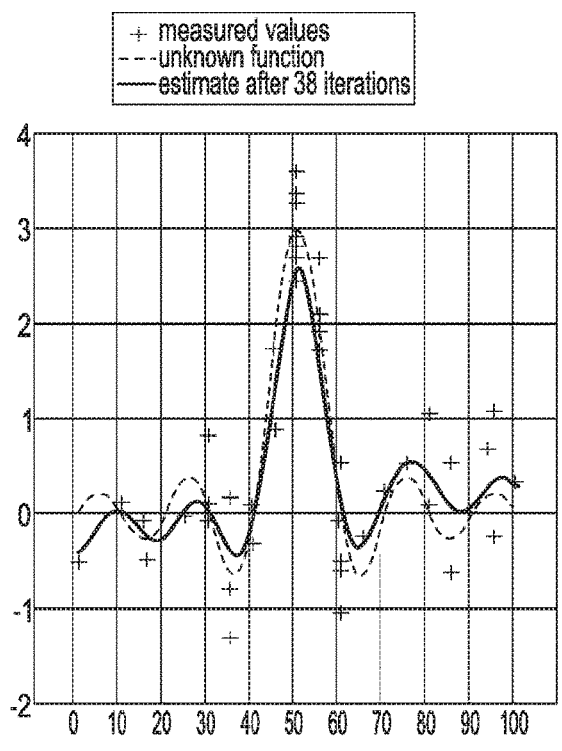
FIG. 12A is a graph illustrating an unknown function and a function estimate in an example embodiment of the present invention.
Figure 12B:
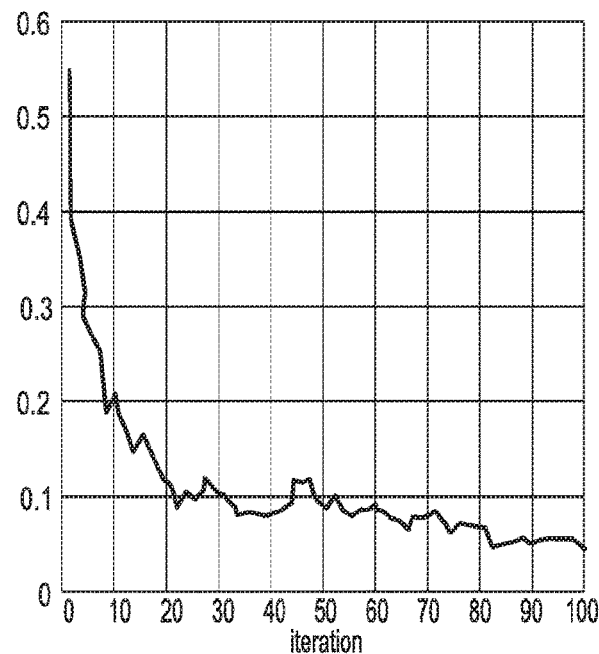
FIG. 12B is a graph illustrating a mean-squared error (MSE) of a function estimate at each iteration with respect to an unknown function, according to an example application of the embodiment of FIG. 12A.
Figure 12C:
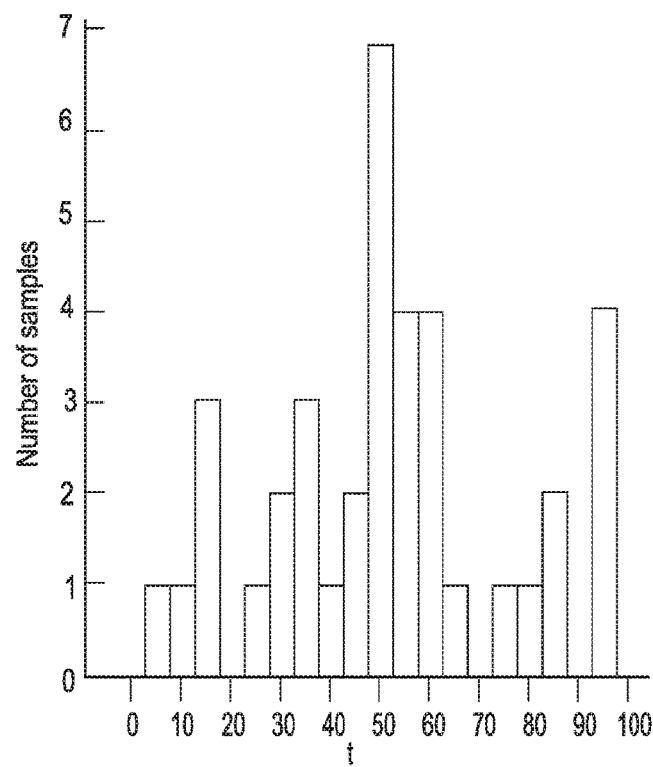
FIG. 12C is a histogram of the assessments selected by the embodiment of FIG. 12A.

For this simulation, $\alpha=3$, $N=101$, and $\sigma=0.5$. The example application begins by collecting eleven equally spaced samples at t={1, 11, ..., 101}. Optimal samples are then selected for an additional 100 iterations. The results are shown in FIGS. 12A-C. The estimated and true functions are shown in FIG. 12A. The mean-squared error (MSE) between the estimated and true functions (FIG. 12B) approaches a low asymptote after approximately 38 iterations, a total of 50 samples gathered over 33 cycles of the function. The 39 sample times selected by the algorithm are shown in FIG. 12A as crosses and their histogram is shown in FIG. 12C. Most samples are concentrated near times corresponding to peaks or valleys of the underlying function.

Example 2—Blood Pressure Measurement

Figure 13A:
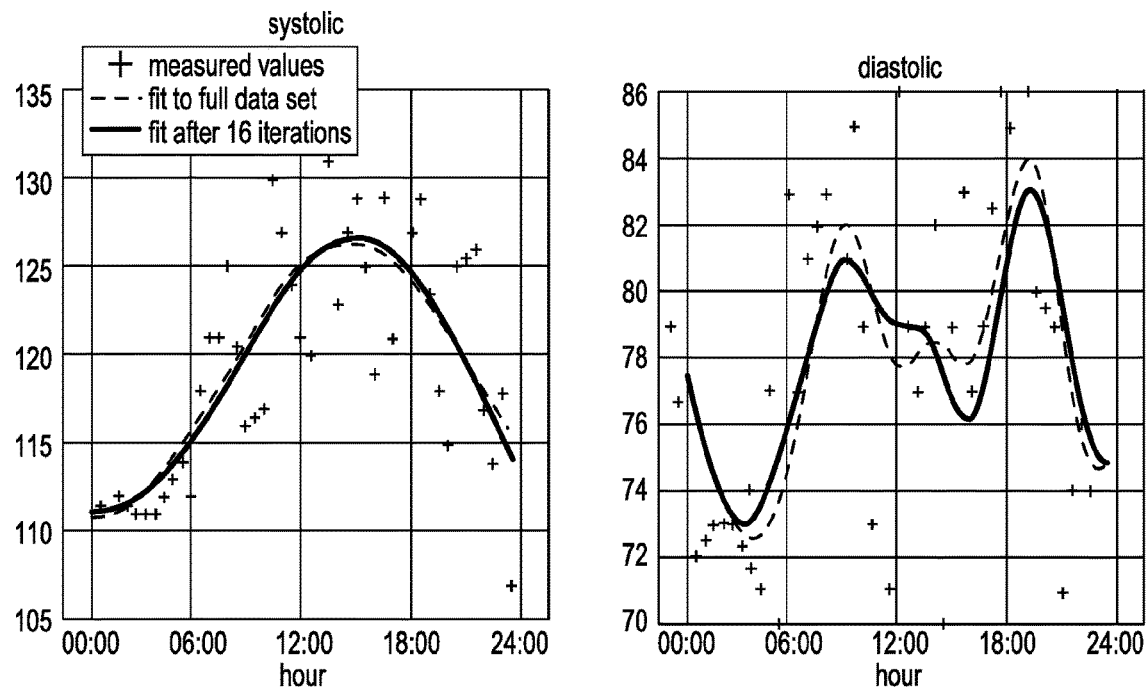
FIG. 13A is a pair of graphs illustrating estimates of systolic and diastolic blood pressure functions in an example embodiment of the present invention.
Figure 13B:
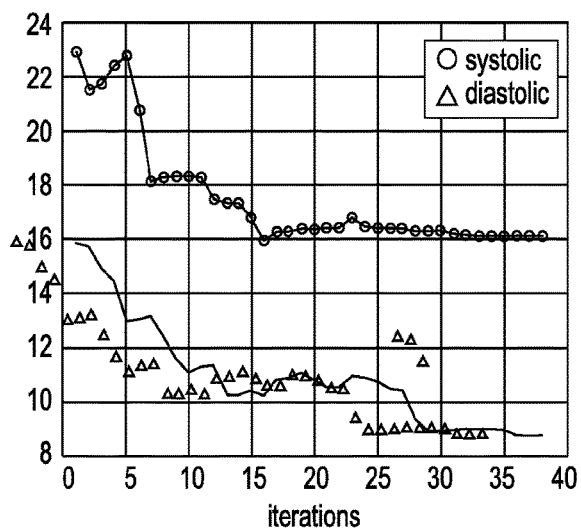
FIG. 13B is a graph illustrating MSE of the function estimates of FIG. 13A at each iteration with respect to the full set of assessments.
Figure 13C:
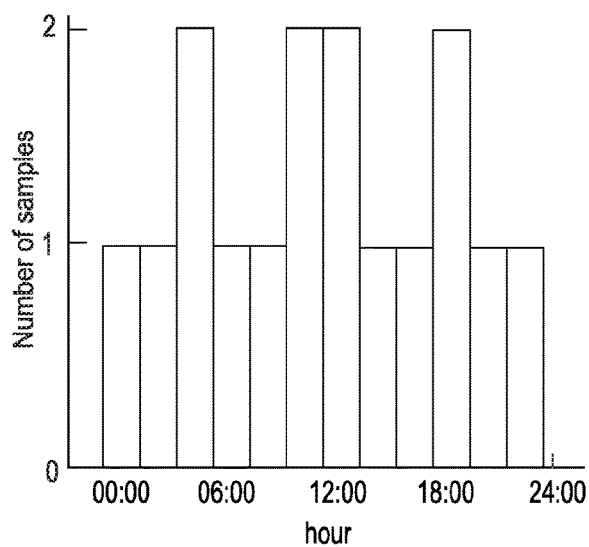
FIG. 13C is a histogram of the assessments selected by the embodiment of FIG. 13A.

In Example 2, measurements of systolic and diastolic blood pressure for a single subject were collected every 30 minutes over a 24-hour period. The data were used to simulate the operation of the disclosed methods and systems. As above, samples were selected as if from successive cycles of the function, i.e., BP as a function of time. Only one data point per 30-minute time interval was selected. The example application begins by obtaining nine samples: every 3 hours from 0:00 to 21:00, and then one sample at 23:30. It then selects optimal sample times until all of the data have been sampled. The results are shown in FIGS. 13A-C. FIG. 13B shows the MSE of the function estimates made at each iteration with respect to the full data set. A low asymptote is approached at 16 iterations, a total of 25 samples over eight cycles (i.e., 24-hour periods) of the function. The function estimates after 16 iterations are shown in FIG. 13A with estimates derived from the full data set for comparison. A histogram of the samples selected per time interval is shown in FIG. 13C.

Example 3—Effect of Drug Treatment for Macular Degeneration

In Example 3, data was collected from twenty subjects who were receiving treatment for macular degeneration in the form of injections of anti vascular endothelial growth factor (antiVEGF). Following the injections, periodic tests were carried out (approximately once every two days over a 90-day period) to measure the effectiveness of the drug in improving the subjects' vision. For the purposes Example 3, one of these tests is shown, the contrast sensitivity function (CSF), which measures the ability of a subject to reliably identify a stimulus (e.g., a letter on a standard vision chart) as a function of its contrast and spatial frequency (i.e., size). Sensitivity is quantified using a standard summary statistic, the area under the log CSF (AULCSF). Each subject's AULCSF is normalized with respect to his or her maximum measured value. All subjects' data are then combined resulting in a set containing measurements at a rate of approximately one per day (shown in FIG. 14A as crosses).

Figure 14A:
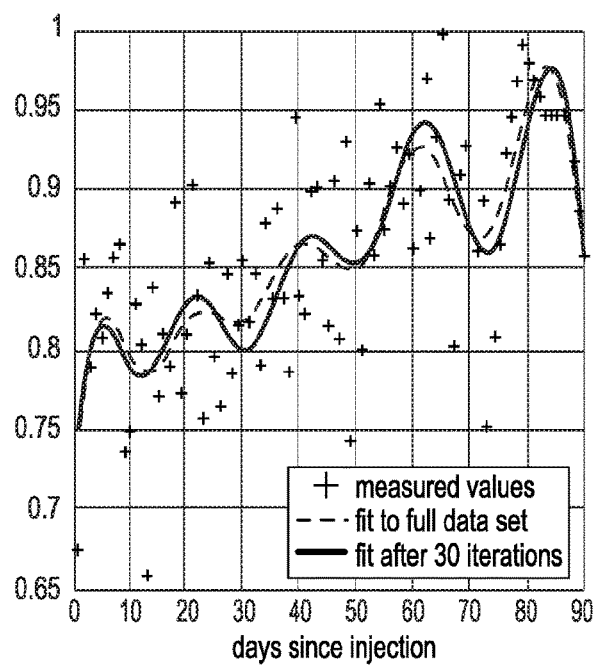
FIG. 14A is a graph illustrating estimates of patients' eye function as a function of days since treatment, according to an example embodiment of the present invention.
Figure 14B:
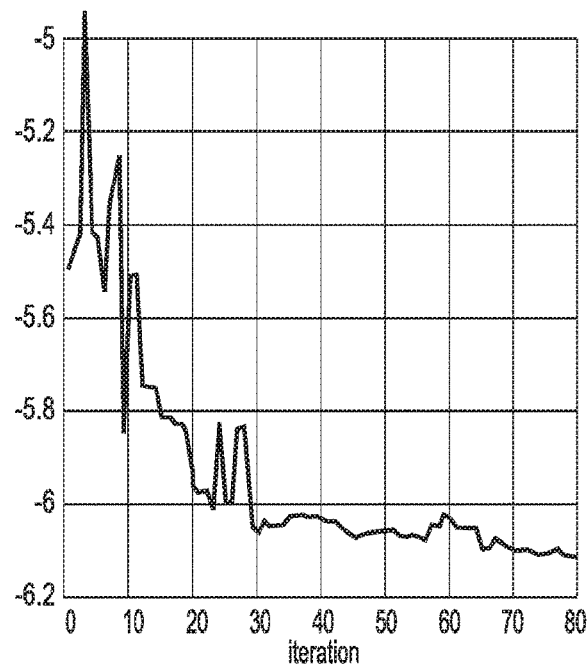
FIG. 14B is a graph illustrating log MSE for the function estimate of FIG. 14A at each iteration with respect to the full set of assessments.
Figure 14C:
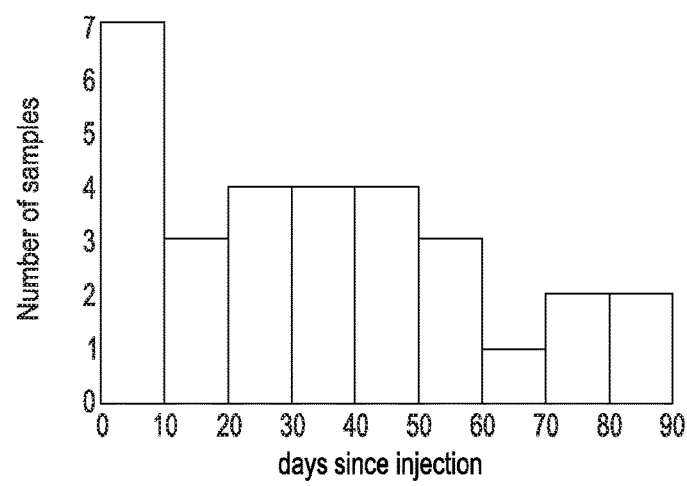
FIG. 14C is a histogram of the assessments selected by the embodiment of FIG. 14A.

Example 3 demonstrates the ability of the disclosed methods and systems to mine an existing data set in order to derive an optimal sampling schedule that can be applied in testing new subjects. Similar to the previous examples, the method/system begins by obtaining ten samples at regular intervals (one every ten days). It then selects an additional 80 optimal samples. The results are shown in FIGS. 14A-C. FIG. 14B shows the log MSE of the function estimates made at each iteration with respect to the full data set. The error approaches a low asymptote at approximately 30 iterations. The function estimate after 30 iterations is shown in FIG. 14A with the estimate derived from the full data set for comparison. FIG. 14C shows the histogram of time points selected, representing a summary of the determined optimal sampling schedule. Samples are selected approximately 1 to 2 days for the first ten days, every 2 to 3 days for the following 50 days, and then every 8 to 10 days in the final 30 days.

Figure 15:
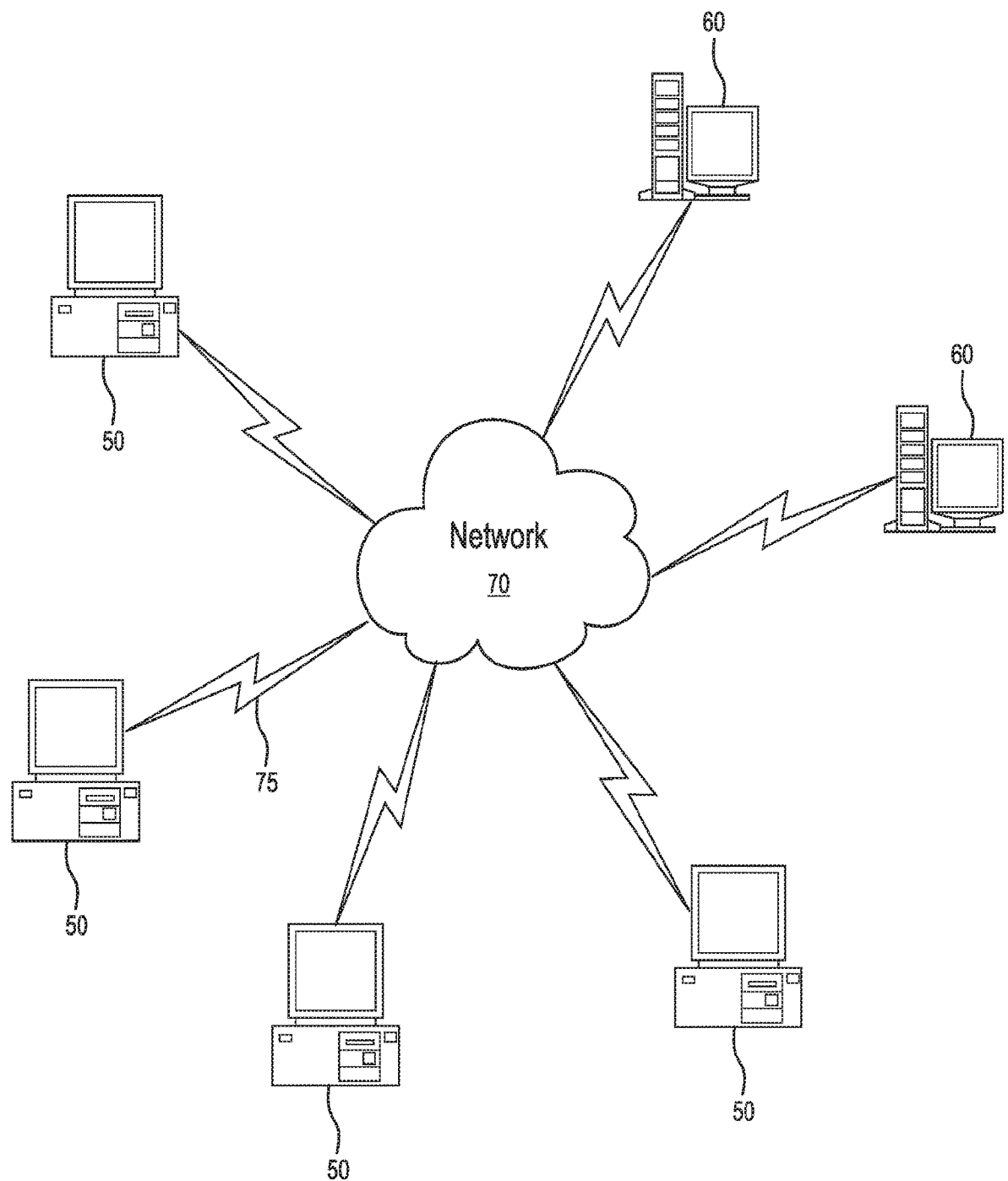
FIG. 15 illustrates a computer network or similar digital processing environment in which embodiments of the present invention may be implemented.

FIG. 15 illustrates a computer network or similar digital processing environment in which embodiments of the present invention may be implemented. Client computer(s)/devices 50 and server computer(s) 60 provide processing, storage, and input/output devices executing application programs and the like. The client computer(s)/devices 50 can also be linked through communications network 70 to other computing devices, including other client devices/processes 50 and server computer(s) 60, via communication links 75 (e.g., wired or wireless network connections). The communications network 70 can be part of a remote access network, a global network (e.g., the Internet), a worldwide collection of computers, local area or wide area networks, and gateways that currently use respective protocols (TCP/IP, Bluetooth®, etc.) to communicate with one another. Other electronic device/computer network architectures are suitable.

Figure 16:
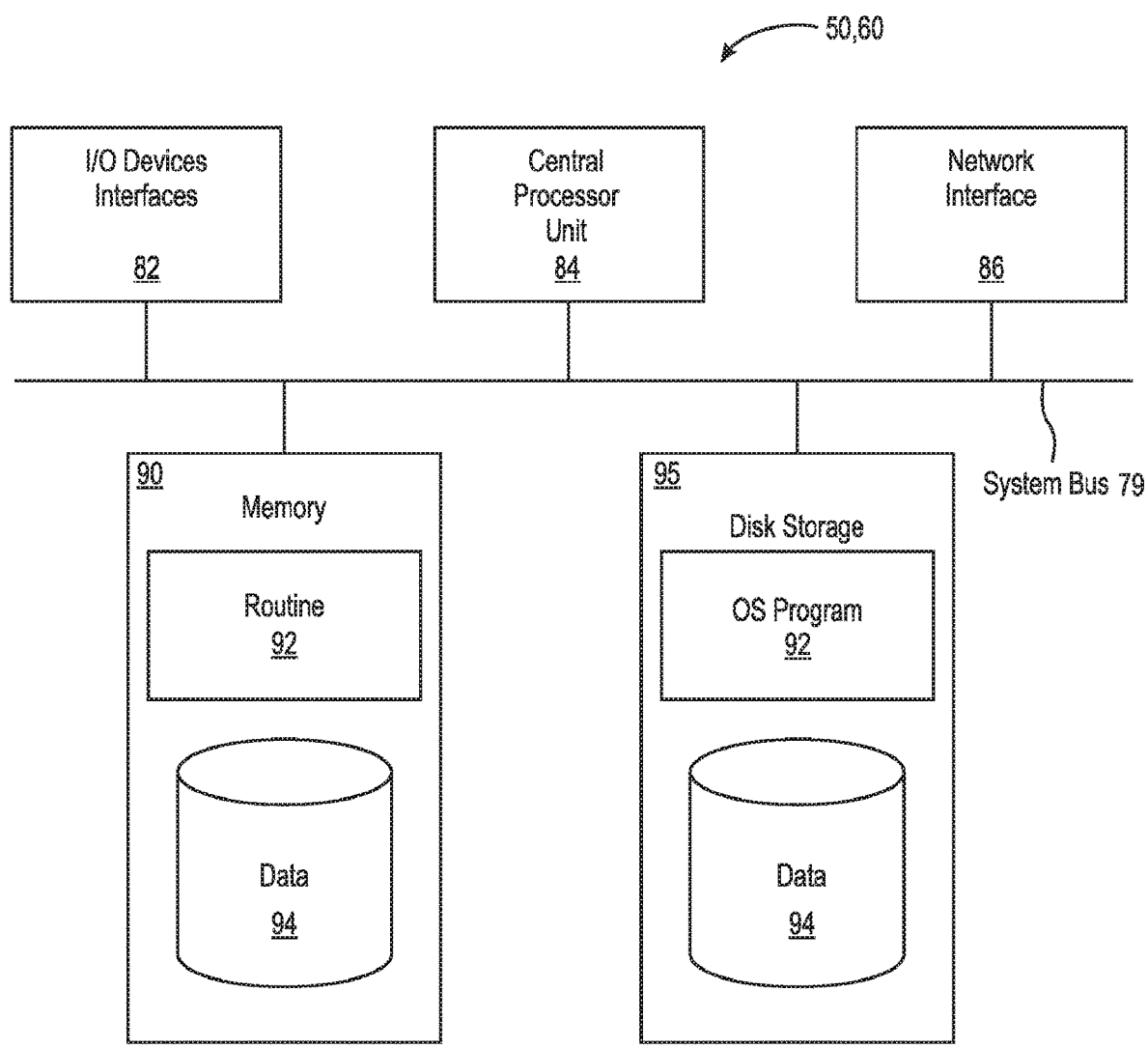
FIG. 16 is a diagram of an example internal structure of a computer in the computer system of FIG. 15.

FIG. 16 is a diagram of an example internal structure of a computer (e.g., client processor/device 50 or server computers 60) in the computer system of FIG. 15. Each computer 50, 60 contains a system bus 79, where a bus is a set of hardware lines used for data transfer among the components of a computer or processing system. The system bus 79 is essentially a shared conduit that connects different elements of a computer system (e.g., processor, disk storage, memory, input/output ports, network ports, etc.) that enables the transfer of information between the elements. Attached to the system bus 79 is an I/O device interface 82 for connecting various input and output devices (e.g., keyboard, mouse, displays, printers, speakers, etc.) to the computer 50, 60. A network interface 86 allows the computer to connect to various other devices attached to a network (e.g., network 70 of FIG. 15). Memory 90 provides volatile storage for computer software instructions 92 and data 94 used to implement an embodiment of the present invention (e.g., selection module, presentation module and labeling module code detailed above). Disk storage 95 provides non-volatile storage for computer software instructions 92 and data 94 used to implement an embodiment of the present invention. A central processor unit 84 is also attached to the system bus 79 and provides for the execution of computer instructions. The disk storage 95 or memory 90 can provide storage for a database. Embodiments of a database can include a SQL database, text file, or other organized collection of data.

In one embodiment, the processor routines 92 and data 94 are a computer program product (generally referenced 92), including a non-transitory computer-readable medium (e.g., a removable storage medium such as one or more DVD-ROM's, CD-ROM's, diskettes, tapes, etc.) that provides at least a portion of the software instructions for the invention system. The computer program product 92 can be installed by any suitable software installation procedure, as is well known in the art. In another embodiment, at least a portion of the software instructions may also be downloaded over a cable communication and/or wireless connection.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of determining an optimal schedule for obtaining assessments of a physical subject, the method comprising:
    obtaining, from a data source over a particular time period, and storing, in memory, a set of assessments of the physical subject, the assessments being of a measurable biological or behavioral quantity of the physical subject;
    determining, by a processor in communication with the memory, and storing, in the memory, a first estimate of a function underlying the measurable quantity, the first estimate being derived from a first subset of values of the measurable quantity of the physical subject over the particular time period based on the set of assessments;
    determining, based on the first estimate of the function, a maximum likelihood estimate for the measurable quantity at at least one time point distinct from time points corresponding to the first subset of values;
    determining, by the processor, and storing, in the memory, a second estimate of the function underlying the measurable quantity, the second estimate being derived from the first subset of values and at least one additional value of the measurable quantity of the physical subject over the particular time period based on the set of assessments and the maximum likelihood estimate;
    comparing, by the processor, the first estimate of the function with the second estimate of the function as a function of time to obtain and store, in the memory, a Kullback-Leibler Divergence (KLD) for the time points during a particular time period that it is possible to obtain an assessment of the physical subject;
    determining a set of KLDs, including the KLD, based on subsequent estimates of the function underlying the measurable quantity and comparison of the subsequent estimates with the first estimate of the function;
    determining, by the processor, and storing, in the memory, a schedule to obtain assessments of the physical subject based on the set of KLDs; and
    configuring testing equipment to obtain samples as a function of the schedule.

2. A method as in claim 1 further comprising:
    determining a value of the measurable quantity corresponding to a maximum KLD out of the set of KLDs;
    updating the first subset to include the value of the measurable quantity to generate an updated subset;
    determining a plurality of estimates of the function underlying the measurable quantity based on the updated subset;
    determining a subsequent set of KLDs based on the plurality of estimates of the function underlying the measurable quantity and a comparison among the plurality of estimates; and
    determining a subsequent value of the measurable quantity corresponding to a subsequent maximum KLD out of the set of KLDs.

3. A method as in claim 1 wherein the particular time period is based on knowledge of the physical subject.

4. A method as in claim 1 wherein the set of assessments of the physical subject are distributed over the particular time period based on knowledge of the physical subject.

5. A method as in claim 1 wherein the data source includes a sensor in communication with the physical subject, the sensor configured to measure the biological or behavioral quantity of the physical subject.

6. A method as in claim 1 wherein the data source is an existing data set including information about the physical subject, and obtaining the set of assessments includes mining the set of assessments from the existing data set.

7. A method as in claim 1 further comprising transmitting the schedule to the testing equipment, the testing equipment being in communication with the physical subject.

8. A method as in claim 1 further comprising causing testing equipment to obtain, in accordance with the schedule, a subsequent assessment of the measurable biological or behavioral quantity of the physical subject.

9. A method as in claim 1 wherein determining the first estimate of values and the second estimate of values includes calculating a Gaussian Process Regression.

10. A system for determining an optimal schedule for obtaining assessments of a physical subject, the system comprising:
    memory;
    a data source;
    a hardware processor in communication with the memory and the data source and configured to perform a predefined set of operations in response to receiving a corresponding instruction selected from a predefined native instruction set of codes, the operations comprising:
        obtaining, from the data source, over a particular time period and store, in the memory, a set of assessments of the physical subject, the assessments being of a measurable biological or behavioral quantity of the physical subject;
        determining and storing, in the memory, a first estimate of a function underlying the measurable quantity, the first estimate being derived from a first subset of values of the measurable quantity of the physical subject over the particular time period based on the set of assessments;
        determining, based on the first estimate of the function, and store, in the memory, a maximum likelihood estimate for the measurable quantity at at least one time point distinct from time points corresponding to the first subset of values;
        determining and storing, in the memory, a second estimate of the function underlying the measurable quantity, the second estimate being derived from the first subset of values and at least one additional value of the measurable quantity of the physical subject over the particular time period based on the set of assessments and the maximum likelihood estimate;
        comparing the first estimate of the function with the second estimate of the function as a function of time to obtain and storing, in the memory, a Kullback-Leibler Divergence (KLD) for the time points during a particular time period that it is possible to obtain an assessment of the physical subject;
        determining a set of KLDs, including the KLD, based on subsequent estimates of the function underlying the measurable quantity and comparison of the subsequent estimates with the first estimate of the function;
        determining and storing, in the memory, a schedule to obtain assessments of the physical subject based on the set of KLDs; and configuring testing equipment to obtain samples as a function of the schedule.

11. A system as in claim 10 wherein the second and fourth set of machine codes cause the hardware processor to determine the first estimate of values and the second estimate of values using Gaussian Process Regression.

12. A system as in claim 10 wherein the operations further include:
determining a value of the measurable quantity corresponding to a maximum KLD out of the set of KLDs;
updating the first subset to include the value of the measurable quantity to generate an updated subset;
determining a plurality of estimates of the function underlying the measurable quantity based on the updated subset;
determining a subsequent set of KLDs based on the plurality of estimates of the function underlying the measurable quantity and a comparison among the plurality of estimates; and
determining a subsequent value of the measurable quantity corresponding to a subsequent maximum KLD out of the set of KLDs.

13. A system as in claim 10 wherein the particular time period is based on knowledge of the physical subject.

14. A system as in claim 10 wherein the set of assessments of the physical subject are distributed over the particular time period based on knowledge of the physical subject.

15. A system as in claim 10 wherein the data source includes a sensor in communication with the physical subject, the sensor configured to measure the biological or behavioral quantity of the physical subject.

16. A system as in claim 10 wherein the data source is an existing data set including information about the physical subject, and the first set of machine codes causes the hardware processor to obtain the set of assessments by mining the set of assessments from the existing data set.

17. A system as in claim 10 further comprising a transmitter to transmit the determined next time to testing equipment in communication with the physical subject.

18. A system as in claim 10 wherein the operations further comprise causing testing equipment to obtain, at the determined at least one next time, a subsequent assessment of the measurable biological or behavioral quantity of the physical subject.

* * * * *